US00PP23527P2

(12) United States Plant Patent
Saul

(10) Patent No.: US PP23,527 P2
(45) Date of Patent: Apr. 9, 2013

(54) ***×HEUCHERELLA* PLANT NAMED 'CUMBERLAND'**

(50) Latin Name: *×Heucherella*
Varietal Denomination: Cumberland

(75) Inventor: Richard G. Saul, Cleveland, GA (US)

(73) Assignee: Itsaul Plants LLC, Alpharetta, GA (US)

( * ) Notice: Subject to any disclaimer, the term of this patent is extended or adjusted under 35 U.S.C. 154(b) by 449 days.

(21) Appl. No.: 12/807,553

(22) Filed: Sep. 8, 2010

(51) Int. Cl.
*A01H 5/00* (2006.01)

(52) U.S. Cl. ..... Plt./441

(58) Field of Classification Search ..... Plt./441
See application file for complete search history.

*Primary Examiner* — June Hwu

(74) *Attorney, Agent, or Firm* — Penny J. Aguirre

(57) ABSTRACT

A new cultivar of ×*Heucherella* plant named 'Cumberland', characterized by its foliage that is green in color with burgundy veins, its large ovate-shaped leaves that average 8 cm in length, its white flowers in mid spring, and its tolerance to heat, humidity with good garden performance in the southern regions of the U.S.

2 Drawing Sheets

Botanical classification: ×*Heucherella*.
Cultivar designation: 'Cumberland'.

CROSS REFERENCE TO A RELATED APPLICATION

This application is co-pending with a U.S. Plant Patent Application filed for a plant derived from the same cross in the Inventor's breeding program that is entitled *Heucherella* Plant Named 'Blue Ridge' (U.S. Plant Pat. No. 22,169).

BACKGROUND OF THE INVENTION

The present invention relates to a new and distinct cultivar of ×*Heucherella* and is hereinafter referred to by the cultivar name 'Cumberland'.

The new cultivar was derived from a controlled breeding program conducted by the Inventor in Dahlonega, Ga. with the objective of creating new cultivars of ×*Heucherella* that are heat tolerant and suitable for use in southern regions of the United States. The Inventor made a cross in March of 2008 between an unnamed plant of *Tiarella cordifolia* as the female parent and *Heuchera*×*villosa* 'Pinor Noir' (U.S. Plant Pat. No. 20,434) as the male parent. The Inventor selected 'Cumberland' in April of 2009 as a single unique plant amongst the seedlings that resulted from the above cross.

Asexual reproduction of the new cultivar was first accomplished under direction of the Inventor by in vitro propagation in Alpharetta, Ga. in April of 2009. Asexual reproduction of the new cultivar has shown that the unique features are stable and reproduced true to type in successive generations.

SUMMARY OF THE INVENTION

The following traits have been repeatedly observed and represent the characteristics of the new cultivar. These attributes in combination distinguish 'Cumberland' as a new and unique cultivar of ×*Heucherella*.

1. 'Cumberland' exhibits foliage that is green in color with burgundy veins.
2. 'Cumberland' exhibits large ovate-shaped leaves that average 8 cm in length when mature.

3. 'Cumberland' obtains a height of 15 cm with blooms reaching 30 cm in height.
4. 'Cumberland' exhibits clean white flowers in mid spring that are more typical of *Tiarella* than *Heuchera*.
5. 'Cumberland' exhibits tolerance to heat, humidity, and has performed well in the southern regions of the U.S.

'Cumberland' can be compared to its parent plants, *Tiarella cordifolia* and *Heuchera* 'Pinot Noir'. *Tiarella cordifolia* differs from 'Cumberland' in having green foliage without burgundy veins, white flowers that are tinged with pink and in blooming earlier in the spring. 'Pinot Noir' differs from 'Cumberland' in having flowers that are white in color and tinged with burgundy, reach 46 cm in height and blooming in late spring and in having foliage that reaches 25 cm in height and is burgundy in color with a silver overlay and burgundy veins. 'Cumberland' can be most closely compared to the ×*Heucherella* cultivar 'Fan Dancer' (not patented). 'Fan Dancer' is similar to 'Cumberland' in having green foliage with burgundy veins and in having white flowers. 'Fan Dancer' differs from 'Cumberland' in having leaves that have silver around the burgundy veins and in being less hardy for southern gardeners as *Heuchera*×*villosa* is not in its heritage.

BRIEF DESCRIPTION OF THE DRAWING

The accompanying colored photographs illustrate the overall appearance and distinct characteristics of the new ×*Heucherella*. The photographs were taken of a one year-old plant of 'Cumberland' as grown outdoors in a garden in Georgia. The photograph on FIG. 1 provides a view of the habit and foliage coloration of 'Cumberland' in bloom and the photograph in FIG. 2 provides a close-up view of the foliage of 'Cumberland'. The colors in the photographs are as close as possible with the digital photography and printing techniques utilized and the color codes in the detailed botanical description more accurately describe the new ×*Heucherella*.

DETAILED BOTANICAL DESCRIPTION OF THE PLANT

Figure 1:
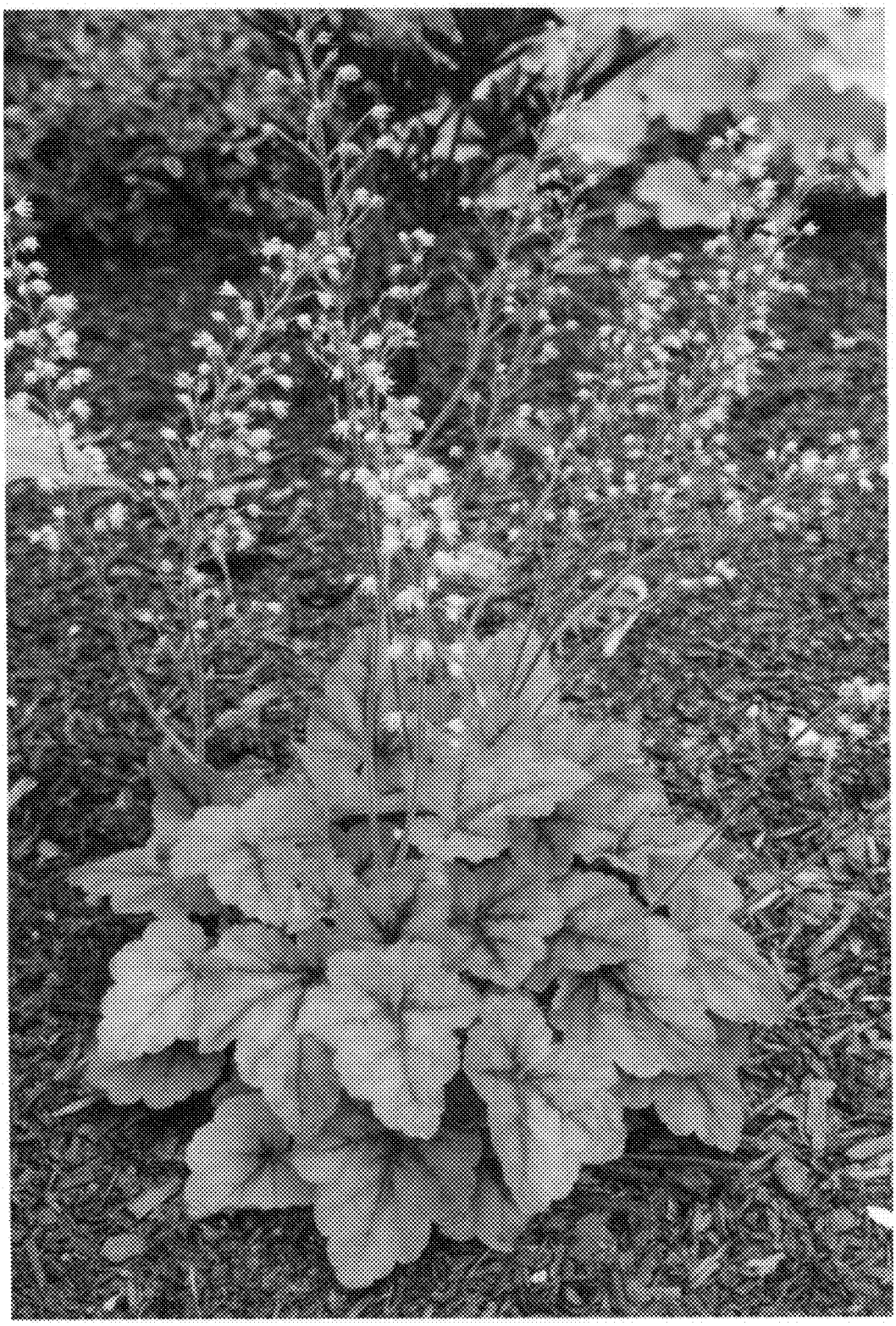
Figure 2:
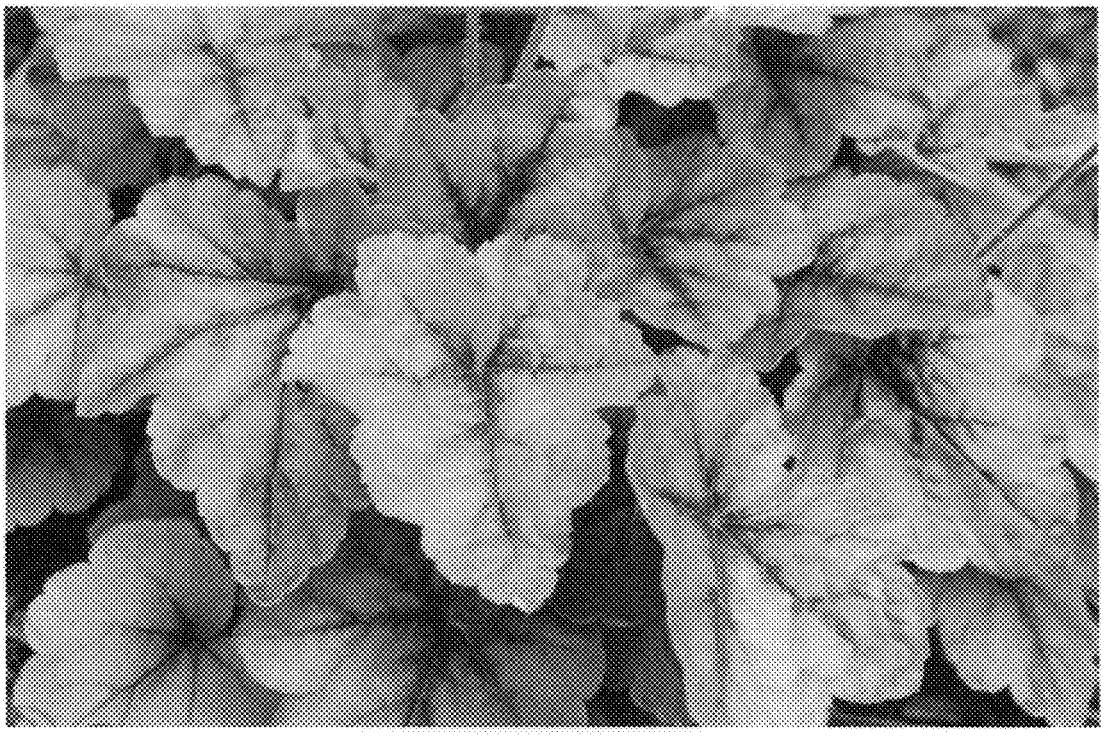

The following is a detailed description of one year-old plants of the new cultivar as grown indoors in one-gallon containers in Alpharetta, Ga. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General description:

*Plant habit*.—Compact, clump-forming herbaceous perennial, mounded foliage.

*Height and spread*.—Reaches about a height of about 12 to 15 cm in height (30 cm bloom) and about 20 cm in width in a one-liter container.

*Blooming period*.—3 weeks in mid spring in Georgia.

*Hardiness*.—At least in U.S.D.A. Zones 5 to 9.

*Diseases and pests*.—Disease free in the conditions tested, no susceptibility or resistance to pests has been observed.

*Root description*.—Fibrous roots on woody rootstalks.

*Branching habit*.—Basal rosettes of leaves on petioles.

*Propagation*.—In vitro propagation is the preferred method.

*Growth rate*.—Vigorous.

Foliage description:

*Leaf shape*.—Ovate.

*Leaf division*.—Simple.

*Leaf base*.—Auriculate.

*Leaf apex*.—Acute.

*Leaf venation*.—Primary palmate, secondary net-veined, conspicuous with upper surface N187B maturing to N187A.

*Leaf margins*.—Lobed with 3 to 7 lobes per leaf, lobe margins crenate with abruptly acute tips.

*Leaf attachment*.—Petiolate.

*Leaf arrangement*.—Basal rosettes.

*Leaf orientation*.—Held horizontal to petiole, slightly ruffled.

*Leaf surface*.—Upper surface pubescent with 0.5 mm stiff hairs, lower surface glabrous leaf blade, pubescent veins.

*Leaf color*.—Upper surface emerging 144B in color with veins N187B; upper surface mature 137A in color with veins N187A; lower surface emerging and maturing 194A in color.

*Leaf size*.—An average of 8 cm in length and 6.5 cm in width when mature.

*Leaf quantity*.—About 110 per one-liter container.

*Petioles*.—Round in shape, an average of 4 cm in length; average diameter of 3 mm, 194A in color with a base tinged N77C, surface is densely pubescent.

*Stipules*.—None.

Flower description:

*Inflorescence type*.—Numerous minute actinomorphic flowers arranged on a branched panicle on flower scapes emerging from the base of the rosette.

*Inflorescence size*.—Reaches an average of 20 cm in height and 5 cm in width in full bloom.

*Flower fragrance*.—None.

*Flower quantity*.—Average of 50 flower per inflorescence.

*Flower lastingness*.—Average of 7 days per flower, individual panicles bloom for about 3 weeks, flowers self cleaning.

*Flower buds*.—Globose to obovate, average of 2 mm in diameter and 2 mm in depth, 144B in color.

*Flower aspect*.—Held slightly downward on pedicels held at 45° angle from rachis.

*Flower shape*.—Campanulate, with base implanted in hypanthium where sepals, petals and filaments are fused.

*Flower size*.—Average of 5 mm in length and 4 mm in diameter.

*Petals*.—About 5, narrowly elliptic in shape and emerge from between sepals in hypanthium, margin is entire, apex is abruptly acuminate, about 3 mm in length and 1 mm in width, upper and lower surface is glabrous, color of upper and lower surface when opening and fully opened is NN155C, color of both surfaces fades to N155D.

*Calyx*.—Campanulate, sepals fused at base to 1 mm hypanthium, 5 mm in diameter and 4 mm in depth.

*Sepals*.—5, un-fused portion broadly oblong in shape, average of 3 mm in length and 2 mm in width, margin is entire, apex is broadly acute, based is fused, surface densely villose, color of upper surface; 145A at apex and 145D at base; color of lower surface;138C at apex and 193C at base.

*Peduncles* (*flower scape*).—Average of 30 cm in length and 6 mm in width, color is 144B, surface pubescent, held at about 20° from vertical.

*Rachis*.—Average of 1 cm in length and 1 mm round, densely pubescent, distal end 144B in color and 71A towards base of rosette.

*Pedicels*.—Average of 1.3 cm in length and 1 mm round, densely pubescent, distal end 144B in color, held at 20° to peduncle.

*Gynoecium*.—2 Pistils, club-shaped, about 5 mm in length, stigmas minute and 155C in color, styles are continuous with ovary, about 4 mm in length and 155C in color, ovary is superior and 155C in color.

*Androecium*.—Average of 5 stamens, if present, sometimes vestigial, anthers are ovate in shape, basifixed, about 0.2 mm in length and 155B in color, filaments are 5 mm in length and 155C in color, no pollen was detected.

*Seed*.—Seed development of the new cultivar has not been observed.

It is claimed:

1. A new and distinct cultivar of ×*Heucherella* plant named 'Cumberland' as herein illustrated and described.

* * * * *